Figure 2A:
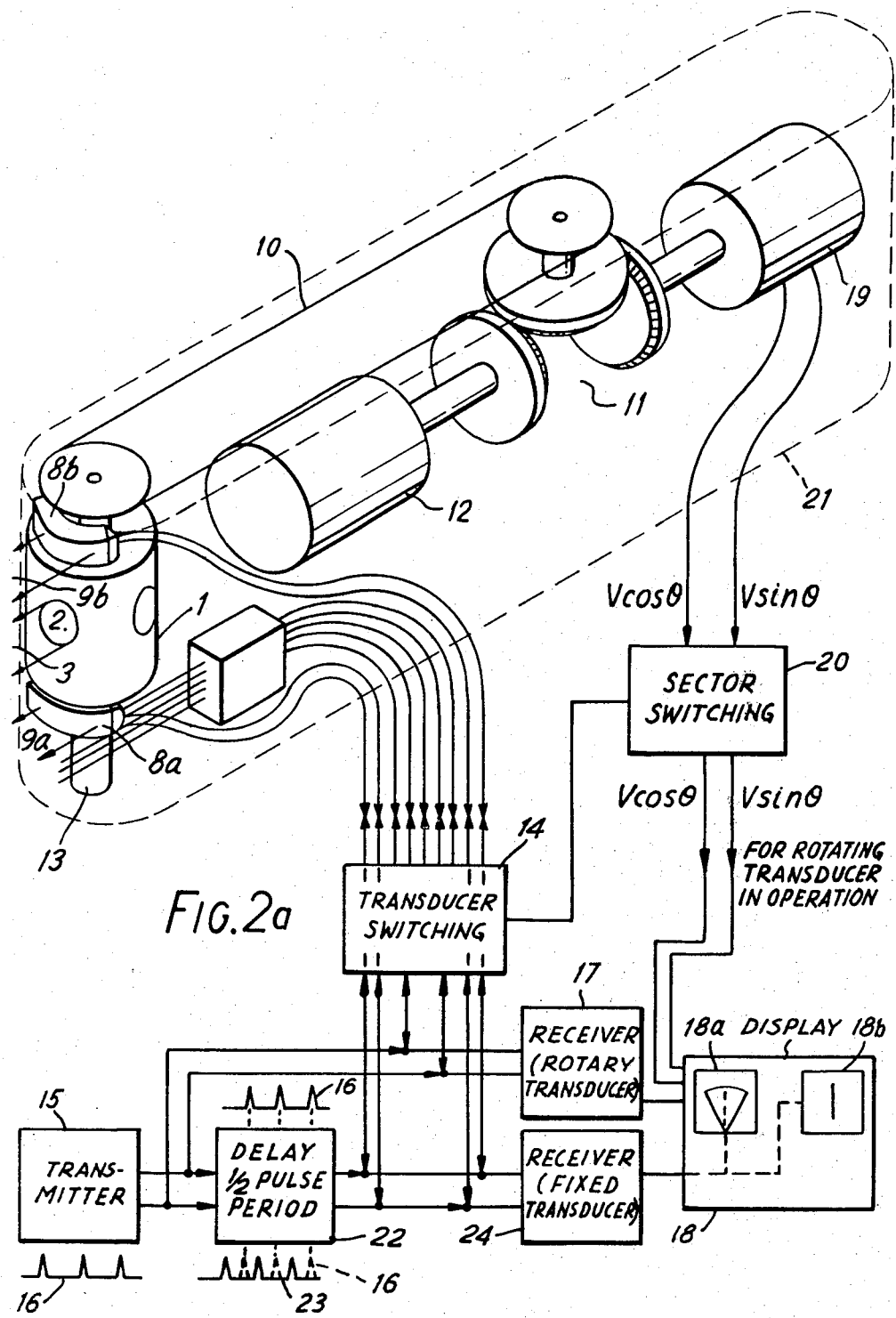

United States Patent [19]

Fraser

[11] 4,228,687
[45] Oct. 21, 1980

[54] ULTRASONIC TRANSDUCERS

[75] Inventor: Brian W. Fraser, Livingston, Scotland

[73] Assignee: EMI Limited, Hayes, England

[21] Appl. No.: 23,344

[22] Filed: Mar. 23, 1979

[30] Foreign Application Priority Data

Mar. 31, 1978 [GB] United Kingdom ............... 12810/78

[51] Int. Cl.³ ...................... G01N 29/04; A61B 10/00
[52] U.S. Cl. ....................................... 73/626; 73/628; 73/641; 128/663
[58] Field of Search ................. 73/620, 621, 625, 626, 73/628, 633, 641; 128/660, 661, 663

[56] References Cited

U.S. PATENT DOCUMENTS

| 3,403,671 | 10/1968 | Flaherty et al. | 73/621 |
| 4,034,744 | 7/1977 | Goldberg | 73/620 |
| 4,078,435 | 3/1978 | Kossoff et al. | 73/621 |
| 4,143,554 | 3/1979 | Nagy et al. | 73/620 |

Primary Examiner—James J. Gill
Attorney, Agent, or Firm—Fleit & Jacobson

[57] ABSTRACT

In a rotating probe ultrasonic system the effective PRF may not be sufficiently high for certain purposes, such as examination of the foetal heart. The invention combines fixed transducers looking at a limited region with a rotating probe scanning over a larger region to give a higher effective PRF in the limited region. The two displays are preferably separate although the display of the larger region may conveniently indicate the location of the limited region.

16 Claims, 4 Drawing Figures

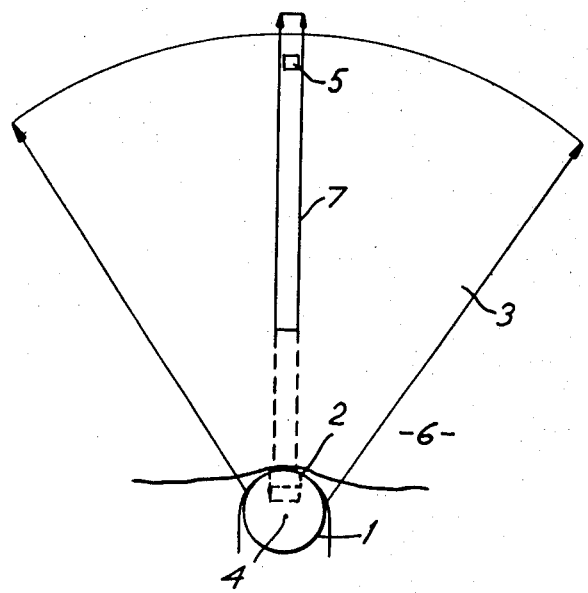
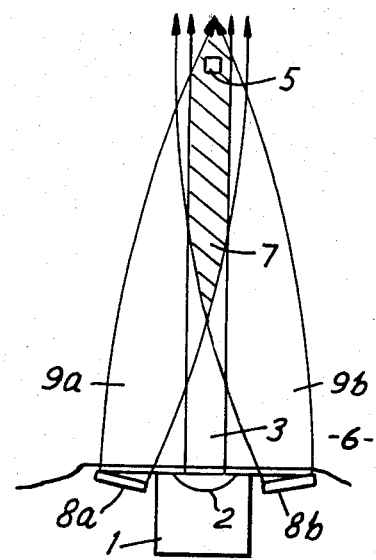
FIG.1a  FIG.1b
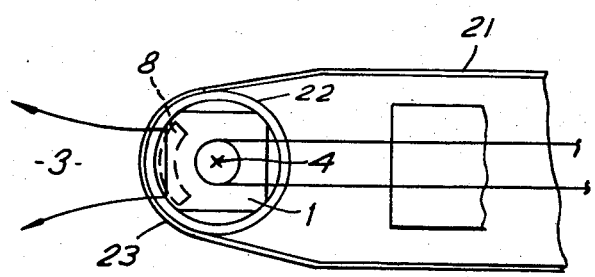
FIG.2b

ULTRASONIC TRANSDUCERS

This invention relates to scanning ultrasonic transducers and is especially, although not exclusively related to arrangements including a rotary scan of a plurality of transducers.

In a typical arrangement of an ultrasonic probe, a plurality of transducers, usually four, are arranged to rotate about a common axis through 360°. The probe head is arranged to bring the transducers into close proximity with the body of a patient to be examined so that the transducers in sequence each sweep a beam of ultrasonic energy through a sector in the body. As each transducer scans the body the beam is pulsed and echoes from within the body are detected for each pulse and further analysed in known manner for display. The transducers share a common transmitter/receiver and are energised in sequence such that only a single transducer facing the body at any time is operative. The display superimposes the outputs from all transducers to show a sector scan at a faster rate than at which an individual transducer is operative. Thus four transducers provide a four times faster scan that one transducer rotating through 360°.

As mentioned the ultrasound is pulsed and the pulse repetition frequency (PRF) is relatively high compared with the scanning rotation. However, because of the slower rotation, any single region of the body is examined at the rotating scan frequency and not the PRF. Thus the effective repetition rate is lower and the ability to show fast movement is limited.

For many purposes that limitation is not serious. However there are many applications in which it is desirable to see fast movements. For instance in examination of pregnant women it is desirable to be able to see the rapid movement of valves in the heart of the foetus. It is however still valuable to provide an area scan since there can be considerable difficulty in accurately locating the heart of a foetus in the womb and in particular in centreing on the heart valves.

It is an object of this invention to provide an improved probe system which is capable of showing rapid movements.

According to the invention there is provided an ultrasonic examination apparatus including first ultrasonic transducer means arranged to scan at least one beam of ultrasonic energy through a sector of a circle centred on the transducer means and to receive ultrasonic energy reflected from reflecting objects disposed within the sector and second ultrasonic transducer means arranged to direct at least one beam of ultrasonic energy to intersect the sector at a region in a constant position relative thereto and to receive ultrasonic energy reflected from reflecting objects disposed in said region.

In order that the invention may be clearly understood and readily carried into effect it will now be described by way of example with reference to the accompanying drawings of which, FIGS. 1a and 1b show the operation of the invention in two orthogonal views and, FIGS. 2a and 2b show an ultrasonic apparatus incorporating the invention in perspective and part plan view respectively.

It is proposed to provide, in conjunction with a multi-transducer rotating system, one or more fixed transducers, the beams of the fixed transducers being related to the sector scan of the rotating transducers. Thus the sector scan may be used to locate accurately the region to be examined for rapid movements and the fixed transducers, having the benefit of, for the same PRF, a more rapid effective repetition rate, can monitor the rapid movement. The transducer can share the same transmitter with interleaved timing to prevent confusion of signals. The receiver and display can be shared but it is desirable to use individual receivers and associated displays. For guidance, however, the position of the fixed beam should be indicated on the display of the sector scan.

For the best effect the fixed transducer should be at the same position as the moving transducers so that the two beams have the same origin. In practice this is not possible but a satisfactory result can be obtained with the fixed transducer in an offset position provided a sufficient intersection is obtained with the sector scan. In this example it is proposed to use two fixed transducers disposed on opposite sides of the moving transducers and having an overlap region, between their respective beams, which intersects the sector scan. Thus the composite effect is that of a fixed transducer at the moving transducer position. More than two fixed transducers can be used to give this effect.

The effect is shown in FIGS. 1a and 1b. FIG. 1a shows at 1 a rotating transducer head with one transducer, 2, providing a substantially planar sector scan 3. It is emphasized that this is not a sector beam but the effect of rotating a narrow beam about rotation axis 4. As discussed the repetition rate of examining pulses is therefore relatively low at reflecting object 5 in the body 6 of the patient being examined. There is also provided therefore a narrow fixed ultrasonic beam 7 which shares the PRF of the rotating beam and has a higher repetition rate at 5.

The means of forming the narrow beam 7 cannot be clearly seen from FIG. 1a. FIG. 1b, however, shows an orthogonal view in which it can be seen that there are two transducers 8a and 8b forming two converging beams 9a and 9b. The converging beams 9a and 9b have an overlap region substantially in the plane of beam 3 and this in effect forms beam 7. It is necessary to take any special steps to restrict the signals received by transducers 8 to the overlap region 7. It is usual and well known with such ultrasonic transducers to effect a range gating on received signals by echo time analysis to allow a sensible display and that will necessarily achieve the desired effect. It may be desired to restrict the displayed signals to those picked up simultaneously by the two transducers 8. Calibration on a test object will suffice properly to relate the two outputs.

FIGS. 2a and 2b show in perspective and part plan view respectively, a practical probe arrangement incorporating the invention. The cylindrical rotating transducer head 1 rotates on an axle on axis 4 on bearings not shown. The cylinder carries four transducers 2, of which one is shown facing outwards of the probe to examine the patient and consequently is emitting the pulsed beam 3. The cylinder is driven by a belt arrangement 10 from a bevel gear arrangement 11 which is in turn driven by a motor 12. Thus motor 12 rotates cylinder 1 about axis 4. The axle also carries a slip-ring/brush assembly 13 which transfers electrical signals between the transducers and the transmitter/receiver circuits. The signals are switched in a transducer switching unit 14 to transfer the electrical signals only to that transducer 2 facing the patient's body. The signals are provided by a conventional transmitter 15 in the form of a pulse train 16 of the chosen PRF. Returned echo signals are applied to a conventional ultrasonic receiver 17 and thence to a display 18.

The bevel gear arrangement 11 also drives an angular resolver of 19 known type to provide V Cos θ and V sin θ signals indicating the progress of the rotation. These are applied to a sector switching unit 20 which switches them at predetermined intervals to apply only to the transducer which is operating. To achieve maximum accuracy the switching can be derived from the sin and cos signals.

Unit 20 also supplies signals to switching unit 14 to synchronise the transducer switching to the progress of the rotation.

The equipment so far described is essentially that of a known rotating probe system and as such is mounted in a casing indicated by the broken outline 21 in FIG. 2a. Some details of the arrangement are shown in FIG. 2b. In particular it can be seen that the cylinder 1 rotates within an inner housing 22 fitted to the end of casing 21. This housing is filled with a liquid transmissive of ultrasound and includes a suitable window 23 for contact with the patient's body.

The housing 22 also includes the fixed transducer 8a and 8b. These are shown in FIG. 2b by the broken outline indicated at 8 so as not to obscure the other details excessively. The transducers, as for transducers 2, may be single piezo-electric ultrasonic transducers of known type, shaped to provide the desired beams. They may also be a plurality of individual transducer elements operated together so as to shape the desired beams. They are fixed in the housing 22 by suitable means not shown, so that they are not disturbed by the motion of the rotating parts but direct fixed beams through window 23 or individual separate windows. In this case as in the case of other features in FIGS. 2a and 2b the fixing means have not been shown so as to not obscure the details of the parts themselves. The provision of means for holding both fixed and rotating parts in the casing 21 is within the abilities of any competent mechanical engineer.

If desired a different transmitter 15 may be used to provide pulses for the operation of transducers 8 than that used for transducers 2. In certain circumstances that could be advantageous. However in this embodiment the pulses for operation of the transducers 8 are derived from the pulse sequence 16 from transmitter 15. They are modified so as to not be simultaneous with the pulsing of transducers 2, (this would also be necessary if different transmitters were used). In this example they are passed through a delay 22, of period equal to half the pulse repetition period, to provide the interleaved pulses 23. They are then provided, without switching in unit 14, to the transducers. Echo signals received by transducers 8 are processed by an individual receiver 24 to provide in the usual manner signals for display at 18. In this example the display 18 comprises two individual display monitors 18a and 18b for the sector (B-scan) and line (A-scan) respectively. Provision is however made to show the position of the A-scan, although not its information, on display 18a to help positioning on the region of interest. The two arrangements may use a common receiver if desired.

It will be realised that the moving transducers shown are not the only arrangement for providing a sector scan. This can be achieved by an electronic scanning multi-element system (phased array). The invention is equally applicable to such alternative sector scan systems.

Although the invention has been described primarily in terms of medical apparatus it will be understood that the invention is applicable to ultrasonic apparatus, for non-medical purposes, which operate in similar manner.

What I claim is:

1. An ultrasonic examination apparatus including first ultrasonic transducer means arranged to scan at least one beam of ultrasonic energy through a sector of a circle centred on the transducer means and to receive ultrasonic energy reflected from reflecting objects disposed within the sector and second ultrasonic transducer means comprising at least two transducers symmetrically disposed about the first transducer means and arranged to co-operate to direct in effect a beam of ultrasonic energy through the sector to intersect the sector at a region in a substantially constant position relative thereto and to receive ultrasonic energy reflected from reflecting objects disposed in said region.

2. An apparatus according to claim 1 in which the second transducer means includes two ultrasonic transducers.

3. An apparatus according to claim 1 in which the first transducer means includes a plurality of ultrasonic transducers arranged to rotate about the centre of said circle to scan respective beams of ultrasonic energy across said sector in succession.

4. An apparatus according to claim 3 in which the first transducer means includes four ultrasonic transducers.

5. An apparatus according to claim 1 including means for operating the first transducer means in pulsed manner, means for operating the second transducer means in pulsed manner and means for arranging the pulses of the two transducer means to be interleaved in time.

6. An apparatus according to claim 5 including a single pulse generator arranged to energise both transducer means in pulsed manner.

7. An apparatus according to claim 1 including a display arrangement for displaying the scenes viewed by the first and second transducer means.

8. An apparatus according to claim 7 in which the display arrangement is adapted to display the two scenes separately.

9. An apparatus according to claim 8 in which the display arrangement is adapted to show, on the display of the scene viewed by the first transducer means, the disposition of the region viewed by the second transducer means.

10. An apparatus according to claim 7 in which the display arrangement is adapted to display the two scenes superimposed.

11. Medical ultrasonic apparatus for examining a substantially planar region of the body of a patient, the apparatus including: first ultrasonic transducer means arranged to scan at least one beam of ultrasonic energy through a sector of a circle, lying in the plane of said region and centred on said first transducer means, and to receive ultrasonic energy reflected from reflecting objects disposed within the sector; and second ultrasonic transducer means arranged to direct at least one further beam of ultrasonic energy in the plane of the sector along a path at a constant position relative to the sector and to receive ultrasonic energy reflected from reflecting objects which are disposed within the sector and in said path; wherein the second transducer means comprises at least one pair of ultrasonic transducers, the transducers of said pair being disposed to direct respective beams of ultrasonic energy from opposite sides of the plane of the region to intersect at said path and thereby to provide in effect said at least one further beam.

12. Medical ultrasonic apparatus according to claim 11 in which the said at least one pair of transducers are symmetrically disposed about the first transducer means.

13. Medical ultrasonic apparatus according to claim 11 in which the second transducer means comprises one pair of tranducers arranged to provide in effect one said further beam.

14. Medical ultrasonic apparatus for examining a substantially planar region of the body of a patient, the apparatus including: ultrasonic transducer means arranged to direct ultrasonic energy along at least one beam and to receive ultrasonic energy reflected from reflecting objects disposed in said beam; means for scanning said at least one beam through a sector of a circle which can be disposed in said plane to examine said region; at least one pair of ultrasonic transducers, arranged to project respective beams of ultrasonic energy, with the transducers of a pair disposed on opposite sides of said sector to direct their respective beams to intersect at a path in, and in a fixed position relative to, said sector to produce the effect of a single beam of ultrasonic energy directed along said path and to receive ultrasonic energy from reflecting objects disposed in said path.

15. Medical ultrasonic apparatus according to claim 14 in which there is provided one said pair of ultrasonic transducers disposed symmetrically about said transducer means to provide in effect a single beam of ultrasonic energy directed along a single said path in said sector.

16. An ultrasonic examination apparatus including ultrasonic means arranged to scan at least one beam of ultrasonic energy through a sector of a circle centred on the transducer means and to receive ultrasonic energy reflected from reflecting objects disposed within the sector and at least one pair of ultrasonic transducers substantially symmetrically disposed aobut the transducer means to direct respective beams of ultrasonic energy to intersect in a region of the said sector, to produce in combination substantially the effect of a single beam of ultrasonic energy directed through said region from the position of the transducer means and to receive ultrasonic energy reflected from reflecting objects disposed in said region.

* * * * *